United States Patent
Privitera et al.

(10) Patent No.: US 7,582,086 B2
(45) Date of Patent: Sep. 1, 2009

(54) SURGICAL CLAMP

(75) Inventors: Salvatore Privitera, Mason, OH (US); James David Hughett, Sr., Liberty Township, OH (US); Kenneth Lance Miller, Hamilton, OH (US)

(73) Assignee: AtriCure, Inc., West Chester, OH (US)

( * ) Notice: Subject to any disclaimer, the term of this patent is extended or adjusted under 35 U.S.C. 154(b) by 694 days.

(21) Appl. No.: 11/254,075

(22) Filed: Oct. 19, 2005

(65) Prior Publication Data

US 2006/0084974 A1 Apr. 20, 2006

Related U.S. Application Data

(60) Provisional application No. 60/620,609, filed on Oct. 20, 2004.

(51) Int. Cl.
*A61B 18/18* (2006.01)
(52) U.S. Cl. .......................... 606/50; 606/205; 606/207
(58) Field of Classification Search ............ 606/50–52, 606/124, 151, 157, 205–208; D24/143; D8/52, 54; 81/418, 176.3, 119, 300, 318; 600/104, 141, 142
See application file for complete search history.

(56) References Cited

U.S. PATENT DOCUMENTS

| | | | | |
|---|---|---|---|---|
| 3,503,396 A | * | 3/1970 | Pierie et al. ................. | 606/207 |
| 4,651,737 A | * | 3/1987 | Deniega ..................... | 606/158 |
| 4,655,216 A | * | 4/1987 | Tischer ....................... | 606/51 |
| 4,730,524 A | * | 3/1988 | Petersen ..................... | 81/367 |
| 5,152,778 A | * | 10/1992 | Bales et al. ................. | 606/205 |
| 5,282,817 A | * | 2/1994 | Hoogeboom et al. ........ | 606/167 |
| 5,331,971 A | * | 7/1994 | Bales et al. ................. | 600/564 |
| 5,408,904 A | * | 4/1995 | Neff ............................ | 81/360 |
| 5,490,819 A | * | 2/1996 | Nicholas et al. ............. | 600/201 |
| 5,618,307 A | * | 4/1997 | Donlon et al. .............. | 606/205 |
| 5,707,377 A | * | 1/1998 | Keller et al. ................ | 606/138 |
| 5,733,295 A | * | 3/1998 | Back et al. .................. | 606/158 |
| 5,792,165 A | * | 8/1998 | Klieman et al. ............. | 606/170 |
| 5,810,881 A | * | 9/1998 | Hoskin et al. ............... | 606/207 |
| 5,843,122 A | * | 12/1998 | Riza ........................... | 606/207 |
| 5,944,723 A | * | 8/1999 | Colleran et al. ............. | 606/88 |
| 6,139,563 A | * | 10/2000 | Cosgrove et al. ............ | 606/205 |
| 6,544,274 B2 | * | 4/2003 | Danitz et al. ................ | 606/157 |

(Continued)

FOREIGN PATENT DOCUMENTS

WO WO 94/05224 3/1994

(Continued)

OTHER PUBLICATIONS

Search Report, PCT/US2005/037748, Feb. 17, 2006, pp. 1-4.

*Primary Examiner*—Linda C Dvorak
*Assistant Examiner*—Amanda Scott
(74) *Attorney, Agent, or Firm*—Cook Alex Ltd.

(57) ABSTRACT

A novel surgical clamp having a pair of jaws, which may be used to ablate or create leisons in tissue. In embodiment, the jaws have an articulated position wherein the jaws are separated and not parallel to one another, an opened position wherein the jaws are separated and substantially parallel to one another, and a closed position wherein the jaws are adjacent and substantially parallel to one another. One or more of the jaws can articulate independent of the other jaw. Other embodiments are described in the attached specification.

13 Claims, 15 Drawing Sheets

U.S. PATENT DOCUMENTS

| | | | |
|---|---|---|---|
| 6,723,109 B2 * | 4/2004 | Solingen | 606/151 |
| 7,087,071 B2 * | 8/2006 | Nicholas et al. | 606/206 |
| 7,108,703 B2 * | 9/2006 | Danitz et al. | 606/157 |
| 7,373,219 B2 * | 5/2008 | Nowlin et al. | 700/245 |
| 2004/0068274 A1 | 4/2004 | Hooven | |
| 2004/0087940 A1 | 5/2004 | Jahns et al. | |

FOREIGN PATENT DOCUMENTS

| WO | WO 02/11623 | 2/2002 |
|---|---|---|

* cited by examiner

SURGICAL CLAMP

RELATED APPLICATIONS

This application claims the benefit of U.S. provisional application No. 60/620,609 filed on Oct. 20, 2004.

BACKGROUND

The present invention relates to surgical instruments, with some embodiments relating clamps, articulated clamps, and tissue ablating clamps. Surgery generally refers to the diagnosis or treatment of injury, deformity, or disease. In a variety of surgical procedures, it is desired to ablated tissue or cause lesions in tissue. Some examples of such procedures include, without limitation, electrical isolation of the pulmonary veins to treat atrial fibrillation, ablation of uterine tissue associated with endometriosis, ablation of esophageal tissue associated with Barrett's esophagus, ablation of cancerous liver tissue, and the like. The foregoing examples are merely illustrative and not exhaustive. While a variety of techniques and devices have been used to ablate or cause lesions in tissue, no one has previously made or used an ablation device in accordance with the present invention. Other aspects of the present teaching relate to novel clamping devices and are not limited to tissue ablation.

BRIEF DESCRIPTION OF DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

In a variety of surgical procedures, it is desirable to ablated tissue or cause lesions in tissue. Tissue ablation can be effected through a variety of different mechanisms known to those skill in the art, such as mono-polar radiofrequency ("RF") energy, bi-polar RF energy, cryogenic techniques, and the like. In clamping arrangements, tissue ablation can be effected through a single jaw of a clamp or through both jaws of a clamp. Tissue ablation will typically be performed once the target tissue is clamped between the closed jaws. One with ordinary skill in the art will recognize that one or more of the foregoing tissue ablation techniques may be employed with the various clamp configurations described below. One with ordinary skill in the art will also recognize advantages of the surgical clamps without tissue ablation functionality. Accordingly, the foregoing examples may or may not include ablation functionality.

Figure 1:
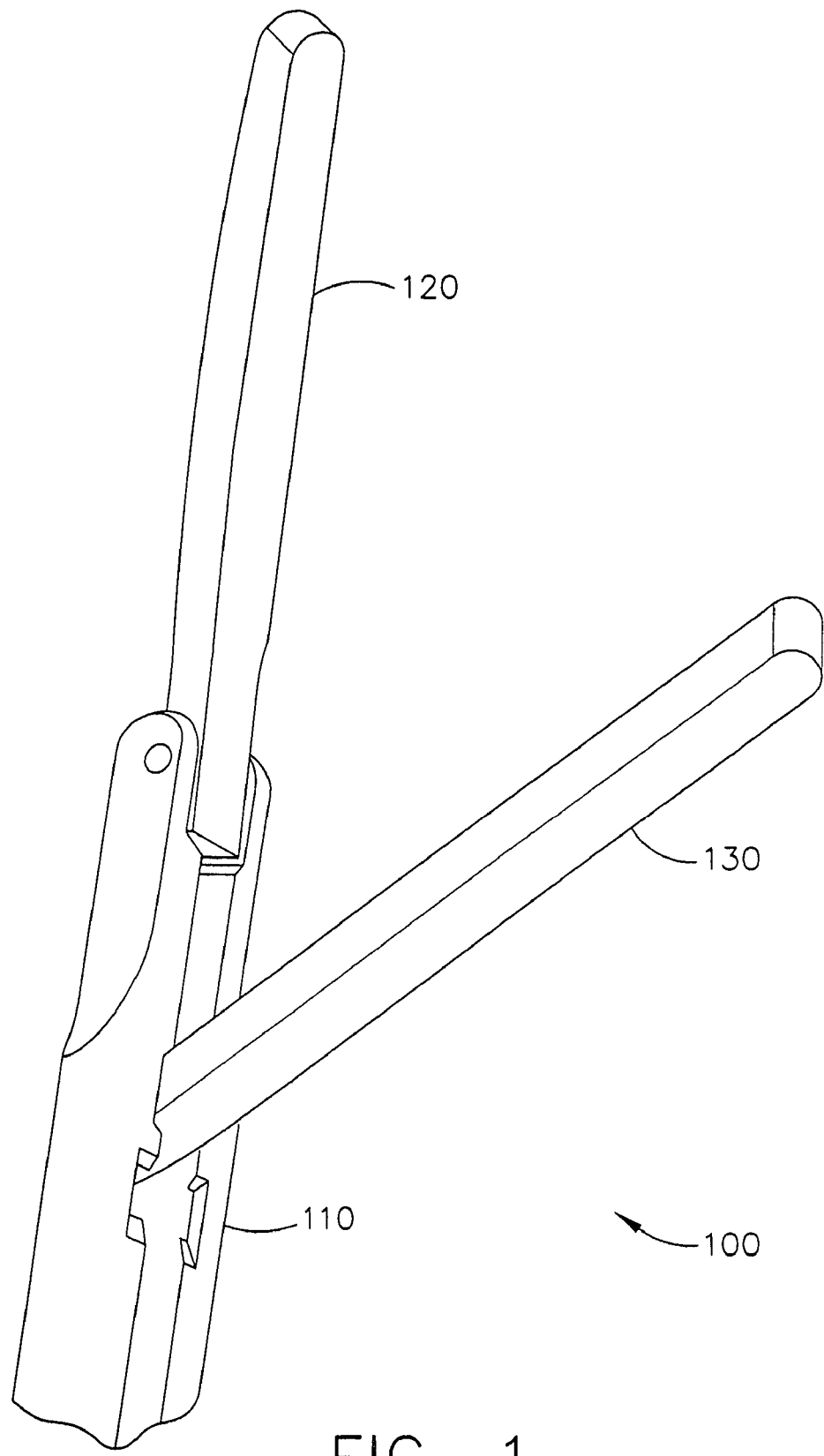
FIG. 1 illustrates an oblique view of an example of an articulated clamp in an articulated position.

FIG. 1 illustrates an example of an articulated clamp (100). The clamp (100) includes a shaft (110), a distal jaw (120), and proximal jaw (130). The shaft could be straight, curved, rigid, flexible, malleable, or articulated. In this embodiment, the jaws are substantially straight; however, the jaws could also be curved in one or more directions. As shown here, the jaws are in an articulated position where the jaws are separated and not parallel to one another. The distal jaw (120) can articulate relative the shaft (110) independent of the proximal jaw (130). As shown here, the distal jaw (120) extends distally relative the shaft (110) and the proximal jaw (130) extends laterally relative the shaft (110). Note that the distal jaw (120) need not be axially aligned the with shaft (110), and likewise the proximal jaw (130) need not extend normal the shaft (110). Instead, angular variations are contemplated, and in many cases may be advantageous based on the anatomy or surgical procedure.

Figure 2:
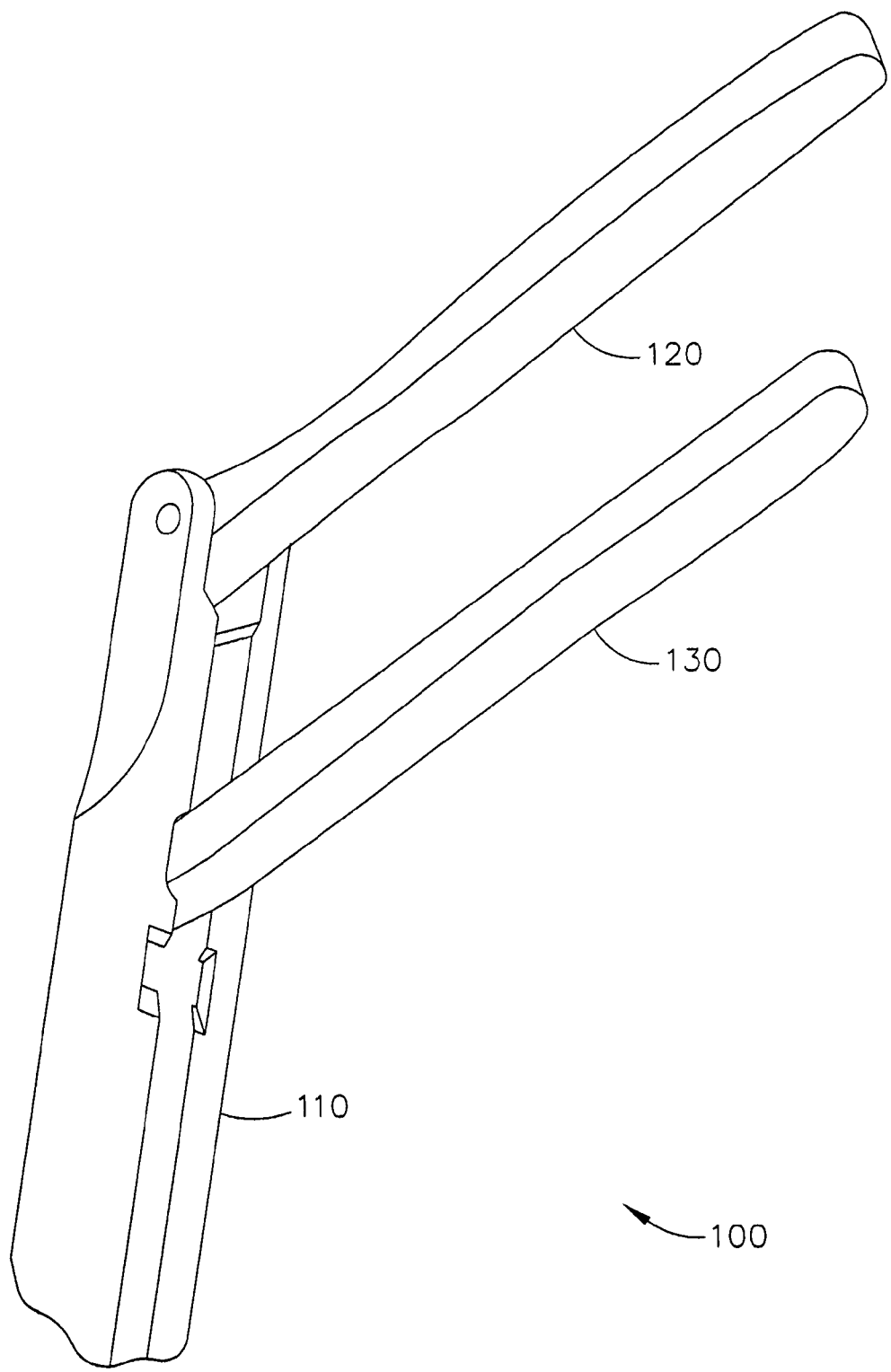
FIG. 2 illustrates an oblique view of the articulated clamp of FIG. 1 in an opened position.

FIG. 2 illustrates the articulate clamp (100) in an opened position where the jaws are separated and substantially parallel to one another. The distal jaw (120) has been articulated such that the distal jaw (120) extends laterally from the shaft (110). The articulation can be passive. For instance, the articulated jaw can be "limp" and readily moveable in response to external forces, such as when pressed against tissue, or resisted by a spring, damper, friction, or other biasing mechanism. Alternatively, the articulation could be active in which the articulation is remotely activated through an actuator (not shown), such as one located on the proximal end of the shaft (110). With active articulation, the jaw is generally rigid and immobile in response to external forces. The jaws can move to a closed position wherein the jaws are adjacent and substantially parallel to one another. As shown in this example, one or both of the jaws will move axially relative to the shaft (110) such that the jaws remain parallel to one another between the opened and closed positions.

Figure 3:
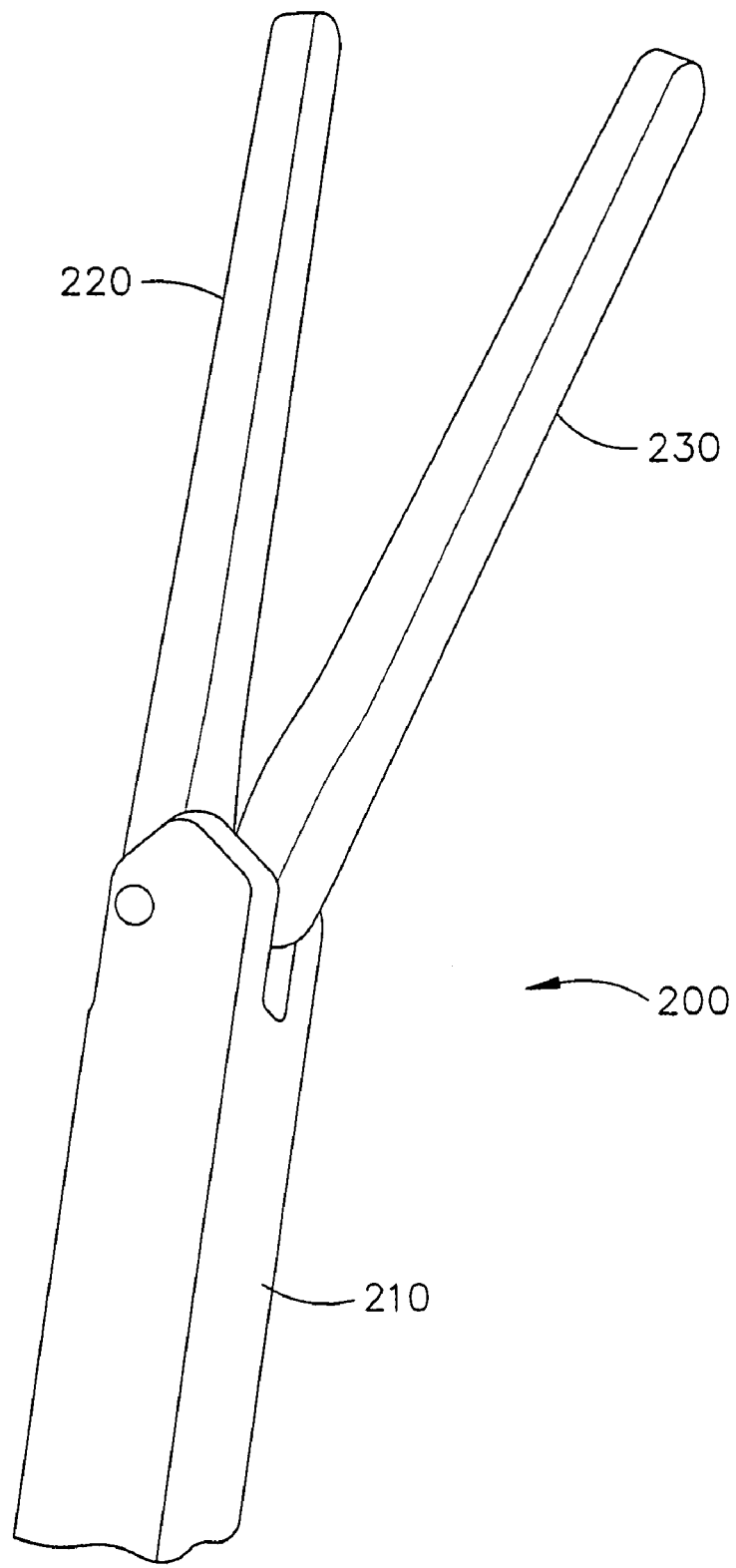
FIG. 3 illustrates an oblique view of an example of an articulated clamp in an opened position.

FIG. 3 illustrates another example of an articulated clamp (200). The clamp (200) includes a shaft (210), a distal jaw (220), and proximal jaw (230). The shaft could be straight, curved, rigid, flexible, malleable, or articulated. In this embodiment, the jaws are substantially straight; however, the jaws could also be curved in one or more directions. Similar to scissors-type motion, the jaw are pivotally moveable relative one another between an opened position and a closed position. As shown here, the jaws are in an opened position where the jaws are separated and not parallel to one another. In the closed position the jaws are pivoted so they are adjacent and parallel to one another. The distal jaw (220), proximal jaw (230), or both may pivot to effect the opening and closing.

Figure 4:
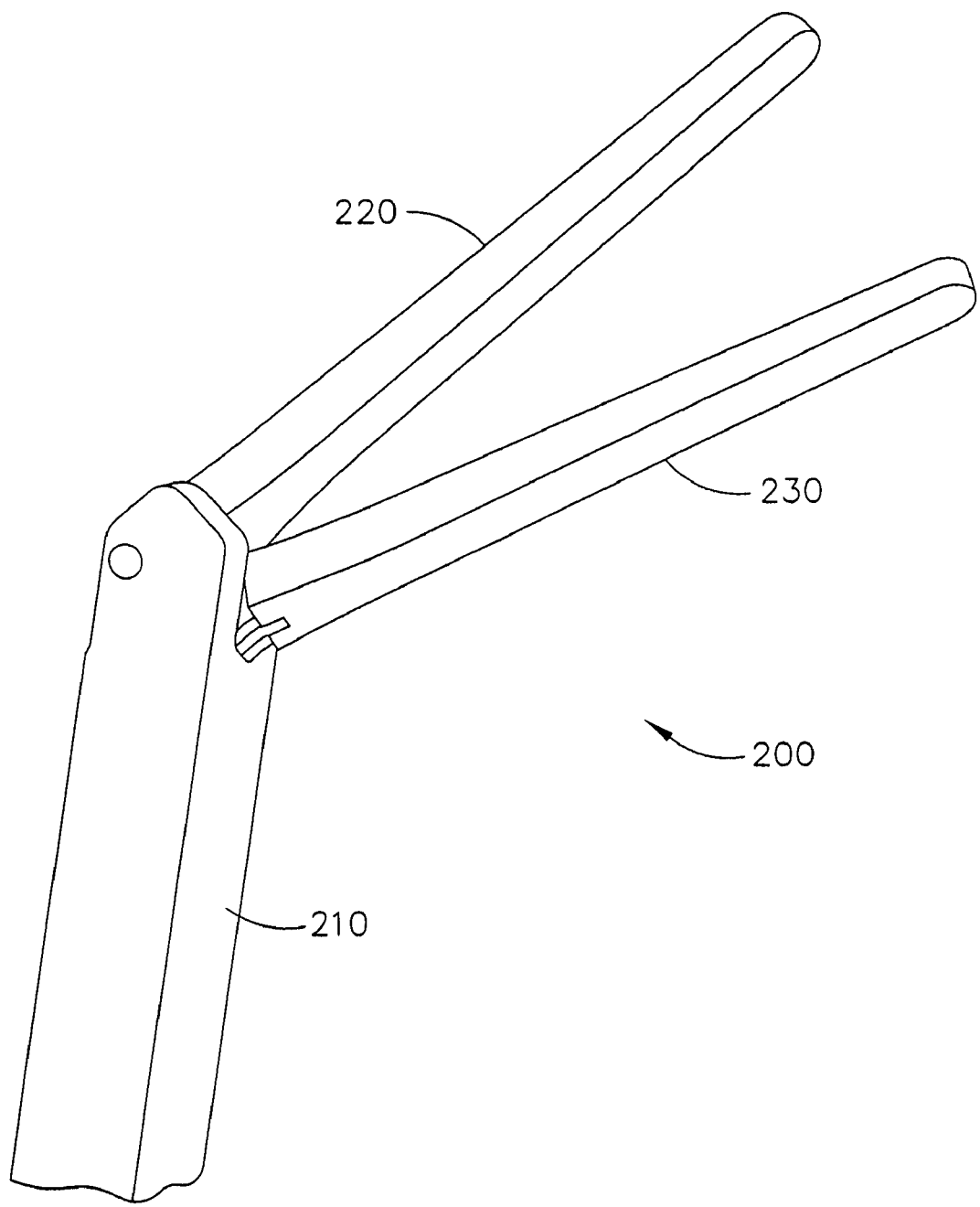
FIG. 4 illustrates an oblique view of the articulated clamp of FIG. 3 in an opened position.

As shown in FIG. 4, the jaws have been articulated relative the shaft (210). In this embodiment, the jaws can be articulated relative the shaft (210) independent of the jaw pivotal motion. Thus, the jaws remain in the opened position but can be articulated. Likewise, the jaws could articulate while the jaws are partially or completely closed. The jaw articulation could extend through a broad range of angles. As shown here, the articulation angle is between 0 and 45 degrees relative the shaft (210); however the articulation range could be much wider. For instance, the jaws could articulate from −90 to +90 degrees relative the shaft (210). The same or different actuator mechanism (not shown) can effect the jaw pivoting and jaw articulation.

Figure 5:
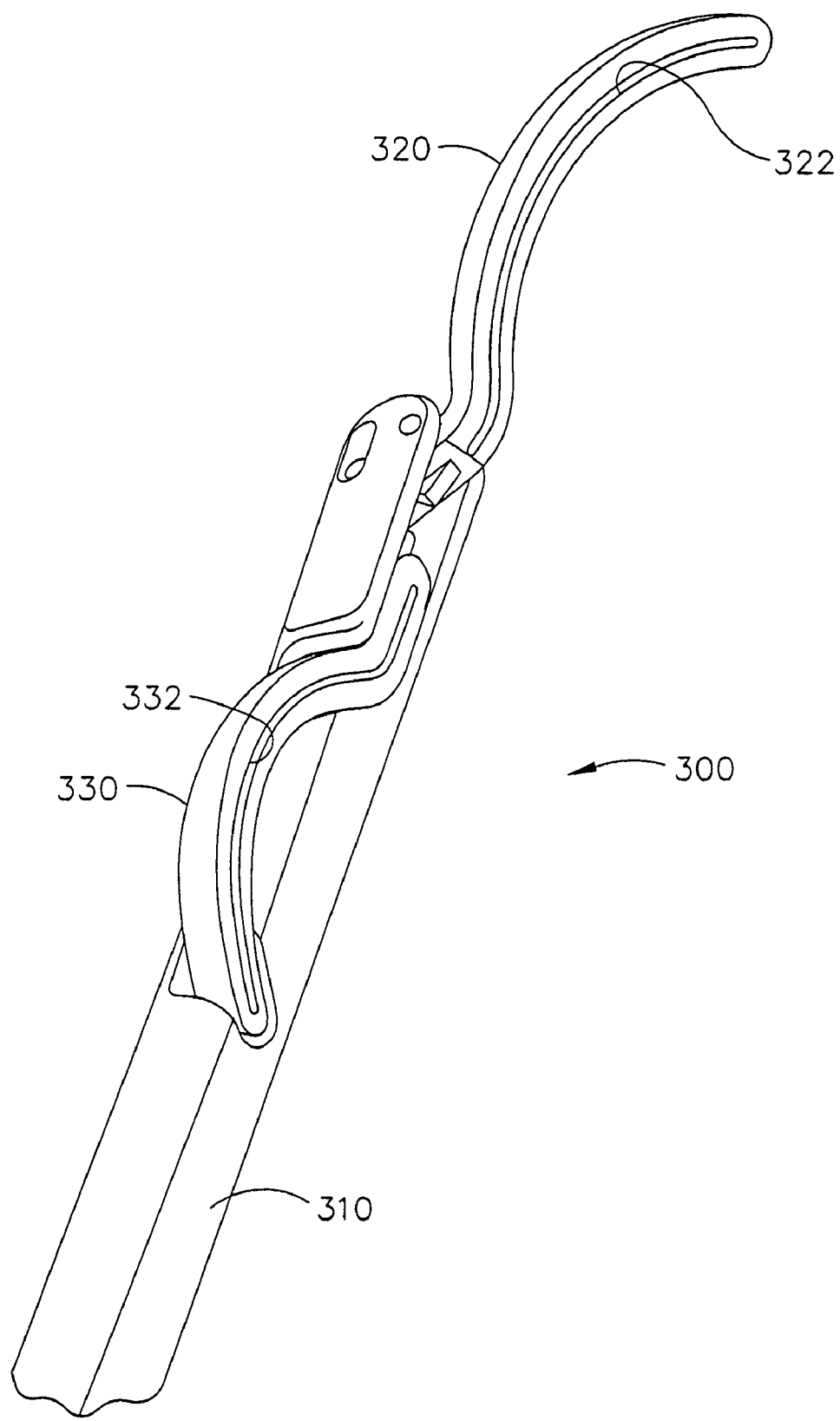
FIG. 5 illustrates an oblique view of an example of an articulated clamp in an articulated position.

FIG. 5 illustrates another example of an articulated clamp (300). The clamp (300) includes a shaft (310), a distal jaw (320), and proximal jaw (330). The shaft could be straight, curved, rigid, flexible, malleable, or articulated. In this embodiment, the jaws are curved; however, the jaws could also be straight or curved in other configurations. As shown here, the jaws are in an articulated position where the jaws are separated and not parallel to one another. As shown here, the distal jaw (320) is extends distally relative the shaft (310) and the proximal jaw (330) extends proximally relative the shaft (310). In the present embodiment, the jaws each have a electrodes (322, 332) to effect tissue ablation through bi-polar or mono-polar RF energy.

Figure 6:
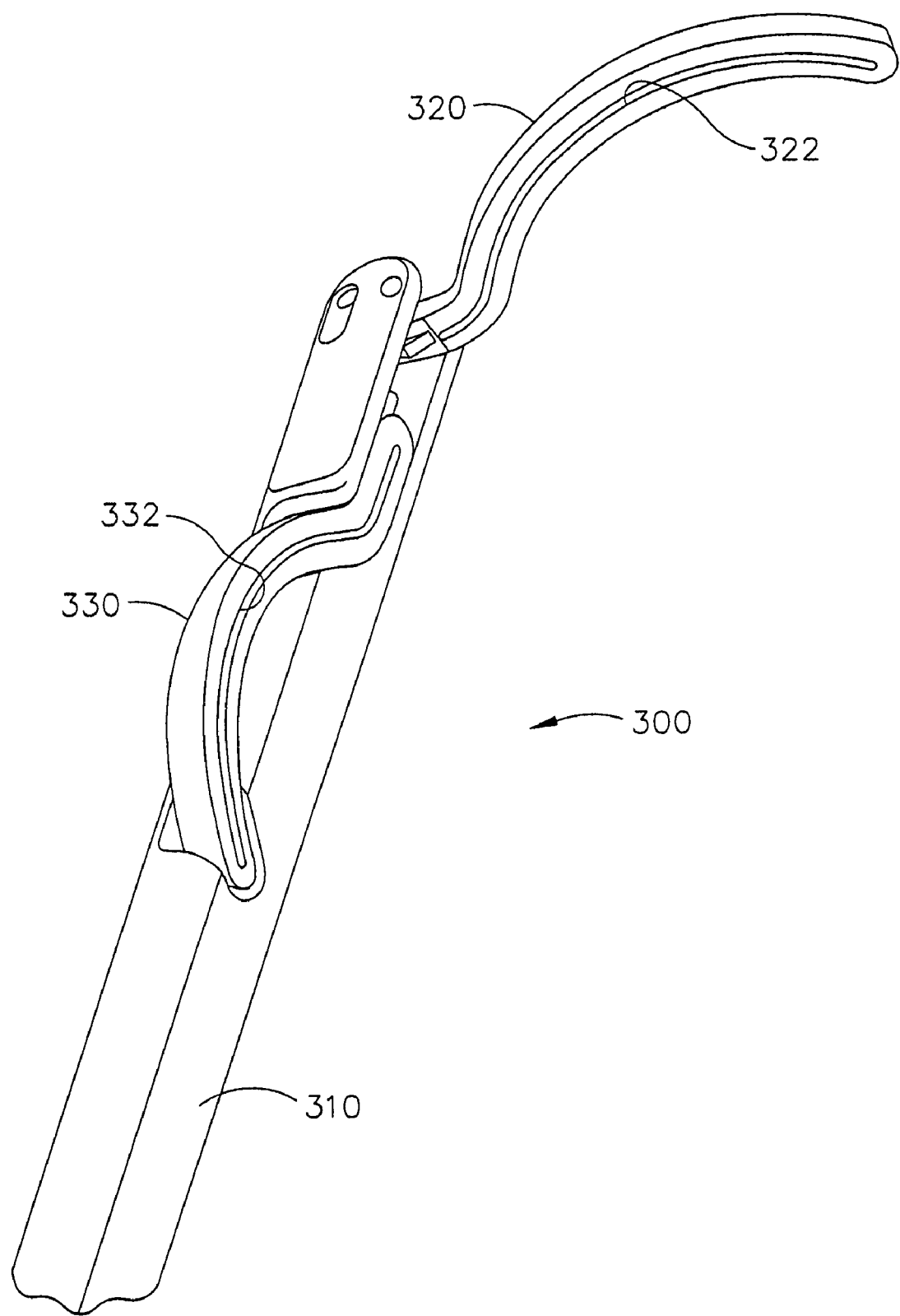
FIG. 6 illustrates an oblique view of the articulated clamp of FIG. 5 in an articulated position.
Figure 7:
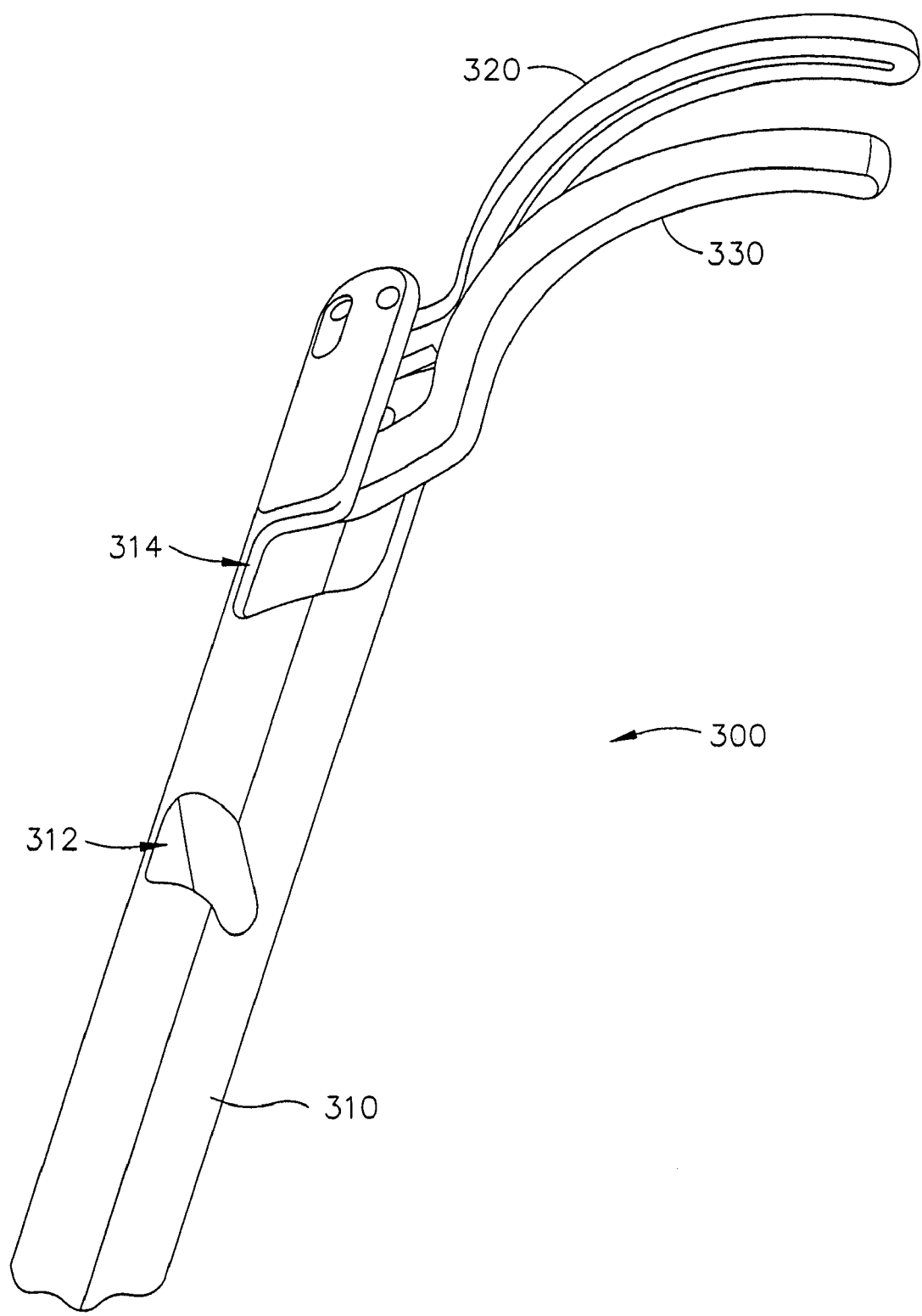
FIG. 7 illustrates an oblique view of the articulated clamp of FIG. 5 in an opened position.

In this embodiment, the distal jaw (320) and proximal jaw (330) articulate relative the shaft (310), either in cooperation with or independent of one another. For instance, FIG. 6 illustrates another articulated position where the jaws are separated and not parallel to one another. The distal jaw (320) has been articulated such that it extends laterally relative the shaft (310), while the proximal jaw (330) has remained unmoved. FIG. 7 illustrates the articulate clamp (300) in an opened position where the jaws are separated and substantially parallel to one another. This view also illustrates recesses (312, 314) in the shaft (310) to receive the proximal jaw (330) when articulated in the fully proximal direction. The proximal jaw (330) has been articulated such that it extends laterally from the shaft (310). The jaws can then move to a closed position wherein the jaws are adjacent and substantially parallel to one another. As shown in this example, one or both of the jaws will move axially relative to the shaft (310) such that the jaws remain parallel to one another between the opened and closed positions.

Note that the distal jaw (320) and/or proximal jaw (330) need not be axially aligned the with shaft (310) in the articulated positions. Likewise, the distal jaw (320) and proximal jaw (330) need not extend normal to the shaft (310) in the opened or closed positions. Instead, angular variations are contemplated, and in many cases may be advantageous based on the anatomy or surgical procedure.

One advantage of articulated clamps (such as embodiments 100, 200, and 300) is the ability to position the jaws near target tissue. This ability is often desirable when operating on or near complicated or sensitive anatomy, or in minimally invasive surgical procedures. As a non-limiting example, the articulated clamp (300) is well suited for open or minimally invasive surgery to treat atrial fibrillation by electrically isolating the left or right pair of pulmonary veins adjacent the left atrium. The articulated jaw positions facilitate positioning the device near the target tissue. The distal and/or proximal jaws may then be articulated to the opened position such that the tissue being treated is interposed between the jaws. The jaws may then be closed and the tissue ablated.

Figure 8:
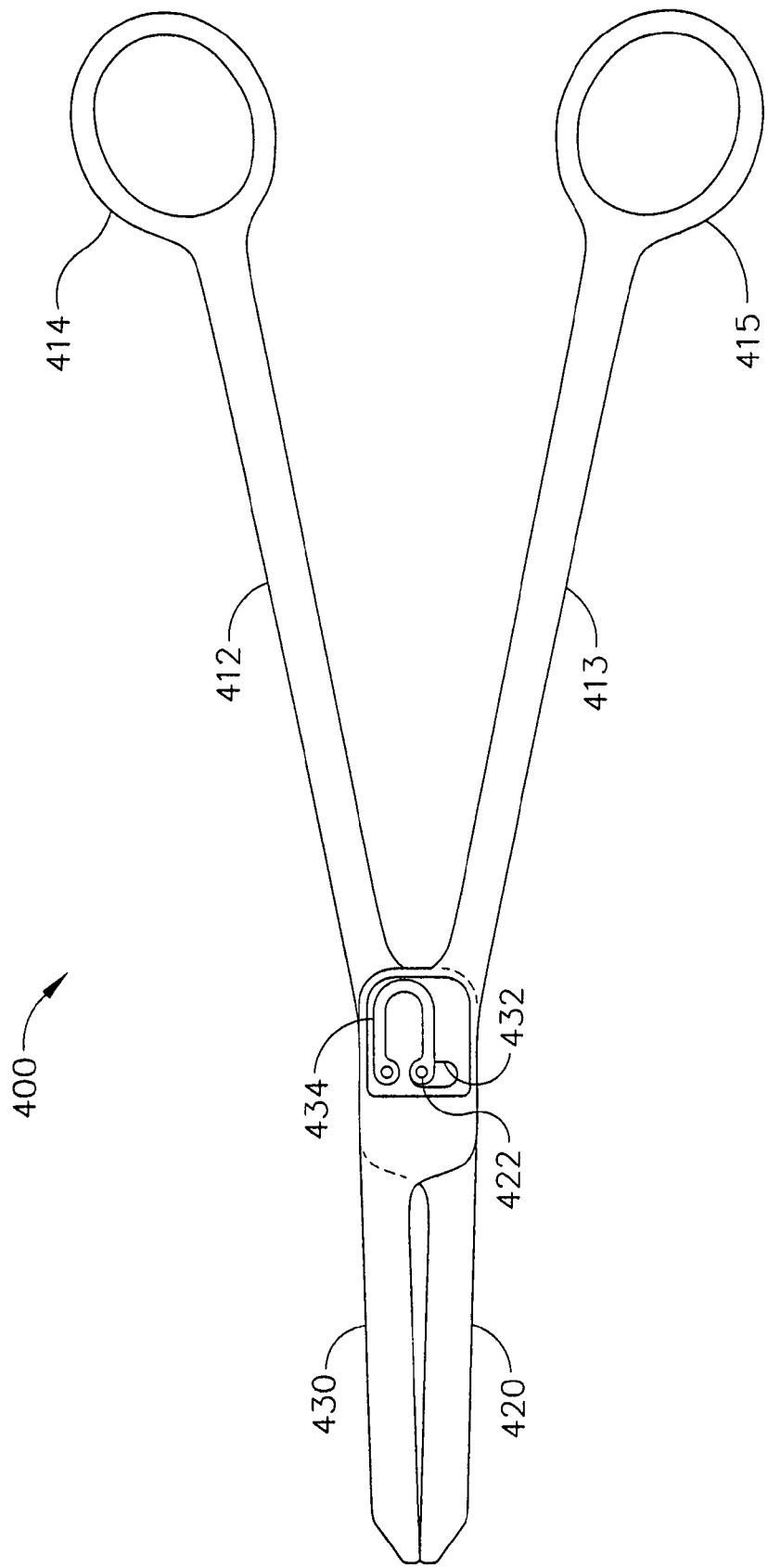
FIG. 8 illustrates a plan view of an example of a clamp with multiple degrees of freedom.

FIG. 8 illustrates an example of a scissor-type clamp (400) with multiple degrees of freedom. The clamp includes two clamp member (412, 413) in crossed relation to each other. Each clamp member has a distal end with a jaw (420, 430) and a proximal end with a handle (414, 415). In this embodiment, the jaws are substantially straight; however, the jaws could also be curved in one or more directions. Preferably, the clamping surfaces of the jaws (420, 430) have tissue ablation functionality, such as mono-polar or bi-polar electrodes. A joint (422) connects the two clamp members (412, 413) where they cross. The joint mates with a lateral slot (432). A biasing mechanism, which in this case is a U-shaped spring (434), biases the jaws (420, 430) towards one another along the lateral slot (432). Thus, this embodiment has two degrees of freedom. The first degree of freedom allows the relative rotation of the two clamp members about the joint. The second degree of freedom allows transverse movement between the two clamp members.

One advantage of this embodiment (400) is the ability to clamp tissue while maintaining a consistant clamping force along the lengths of the jaws. This is especially useful when clamping thicker tissue. The transverse degree of freedom prevents a disproportionate clamping force toward the pivot point of the joint (422). In addition, the spring (434) provides a maximum clamping force, which may be useful in certain procedures or to avoid traumatizing sensitive tissues.

Figure 9:
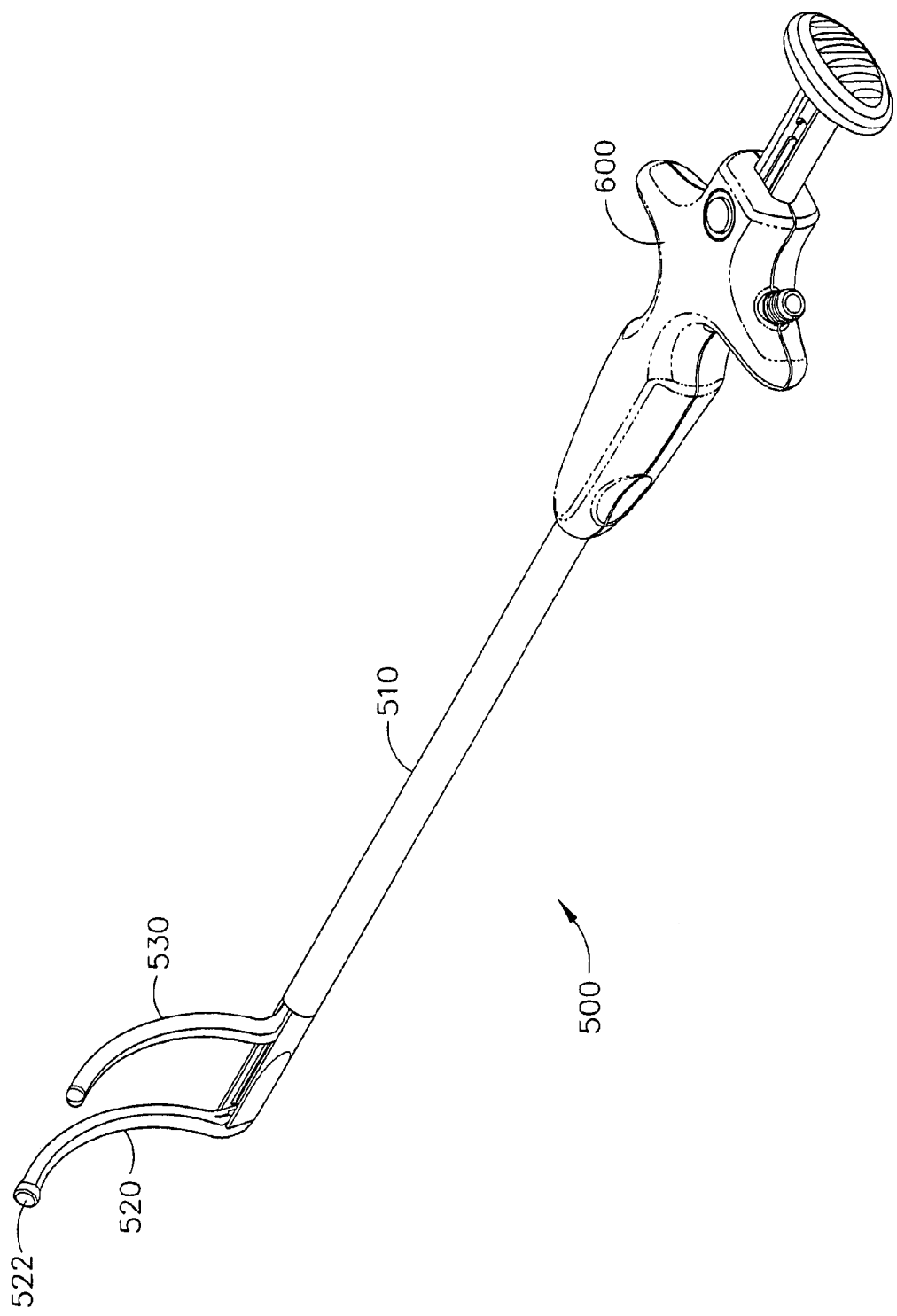
FIG. 9 illustrates an oblique view of an example of an articulated clamp.

FIG. 9 illustrates another example of an articulated clamp (500). This embodiment can be used to create lesions on the heart to treat atrial fibrillation. The clamp (500) includes a shaft (510), a distal jaw (520), a proximal jaw (530), and an handle (600). As shown here, the shaft (510) is straight and rigid; however, it could also be curved, flexible, malleable, or articulated. In the present embodiment, the jaws each have slender electrodes (not shown) on the clamping surfaces to effect tissue ablation through bi-polar or mono-polar RF energy. The jaws are curved; however, the jaws could also be straight or curved in other configurations. As shown here, the jaws are in an opened position where the jaws are separated and parallel to one another. The jaws both extend laterally relative the shaft (510), but not necessarily normal the shaft. The distal jaw (520) can articulate relative the shaft (510) independent of the proximal jaw (530). In this example, the distal jaw (520) can articulate diotally up to about axial alignment with the shaft (510); however, wider or narrower ranges are also contemplated. In this example, the proximal jaw (530) cannot articulate relative the shaft (510). The proximal jaw (530) can move axially along the shaft (510) to a closed position where the jaws are adjacent and substantially parallel to one another. Preferably, the distal jaw (520) will lock in this position parallel to the proximal jaw (530) when the jaws are in the closed position or while the proximal jaw (530) is being moved toward the closed position.

In one variation, the distal jaw (520) is "limp" when articulating. Accordingly, the distal jaw will articulate passively in response to minimal external forces. Optionally, the tip of the distal jaw (520) includes a fastener (522), shown here are a female member, dimensioned to a male fastener counterpart of an instrument guide. For instance, the instrument guide can be an elongate flexible member. When the instrument guide is anchored to the fastener (522), the distal jaw (520) may be positioned to a desired location in the surgical field by pulling the instrument guide. Preferably, the distal jaw (520) will be in its articulated "limp" position so as to reduce interference by surrounding anatomy. The distal and proximal jaws may then be adjusted so that the tissue being treated is interposed between the jaws. The jaws may then be closed and the tissue ablated. After treatment is concluded, and the clamp is opened, the distal jaw will be in its articulated "limp" position, thus pulling the instrument guide until the instrument guide is removed from the surgical field. Examples of instrument guides and exemplary surgical procedures are disclosed in U.S. patent application Ser. No. 11/254,057 filed on even date herewith, the teachings of which are incorporated by reference.

Figure 10:
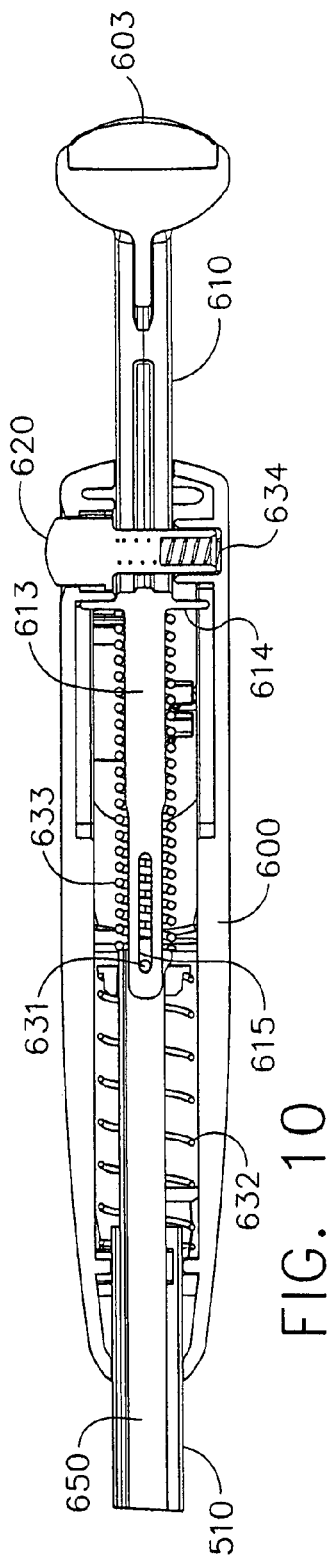
FIG. 10 illustrates a cross-sectional view of the actuator of the articulated clamp of FIG. 9.
Figure 11:
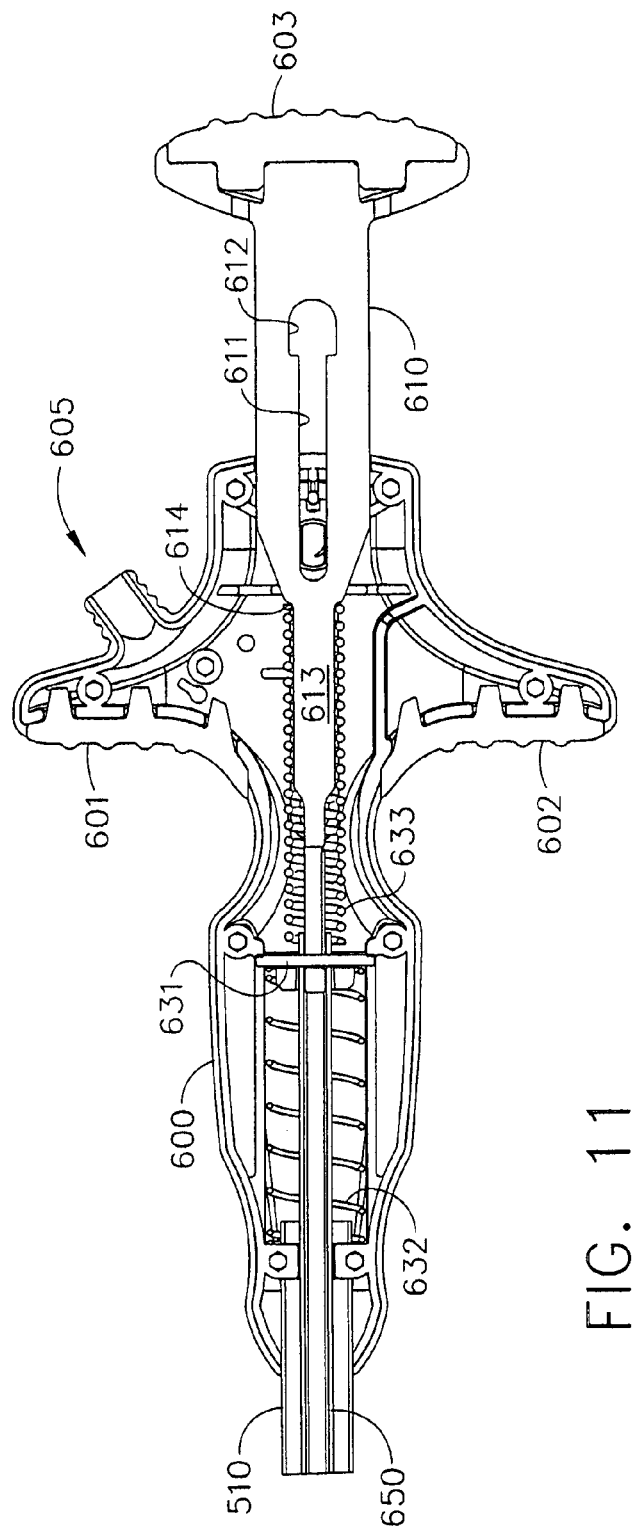
FIG. 11 illustrates a cross-sectional view of the actuator of the articulated clamp of FIG. 9.

FIGS. 10 and 11 illustrates some features of the handle (600). The handle includes grips (601, 602, 603). A port (605) is provided through which wires or tubes may extend from the interior to the exterior of the handle. For instance, wires for the ablation electrodes or sensors on the jaws can be threaded through the shaft (510) into the handle (600) and out through the port (605).

The handle (600) also houses an actuator mechanism. In this example a plunger (610) is used to actuate the jaws. Here, the plunger (610) is aligned with the shaft (510). In the fully retraced or proximal position (as shown), the distal jaw is in its articulated "limp" position. When the plunger (610) is depressed in the distal direction, the distal jaw (520) locks into a position parallel with the proximal jaw (530). Further depression will move the proximal jaw (530) distally towards the closed position. The plunger (610) includes a slot (611) with an opening (612). When the jaws are in the closed position, the opening (612) aligns with the lock (620). A spring (634) forces the lock (620) into the opening (612) preventing the plunger (610) from moving proximally, thus maintaining the jaws in the closed position. Depressing the lock (620) will release the plunger (610) thus allowing proximal movement.

An actuator rod (650) actuates the jaws. Distal movement closes the jaws while proximal movement opens the jaws. The plunger (610) includes a relief rod (613) surrounded in a force limiting spring (633). The force limiting spring (633) is compressed between the step (614) and the actuator rod (650). Depressing the plunger (610) imparts a load on the force limiting spring (633) that is translated to the actuator rod (650), which will move the actuator rod (650) distally. A return spring (632) is operative to move the actuator rod (650) proximally upon releasing the plunger (610). If the jaw clamping load exceeds load of the force limiting spring (633), the slot and pin (615, 631) interface allows the relief rod (613) to move distally without moving the actuator rod (650). Thus, the force limiting spring (633) effectively defines the maximum jaw clamping load. One with ordinary skill in the art will recognize that the tissue clamping pressure if a function of the jaw clamping load and the tissue area being clamped.

While not required, the jaws will preferably move between the opened and closed positions in a 1:1 ratio relative the motion of the plunger (610). Likewise, the jaw clamping load preferably will have a 1:1 ratio relative the depression load on the plunger (610). One advantage of the 1:1 relative ratios of movement and/or load is to improve tactile feedback from the jaws to the surgeon during a surgical procedure.

Figure 12:
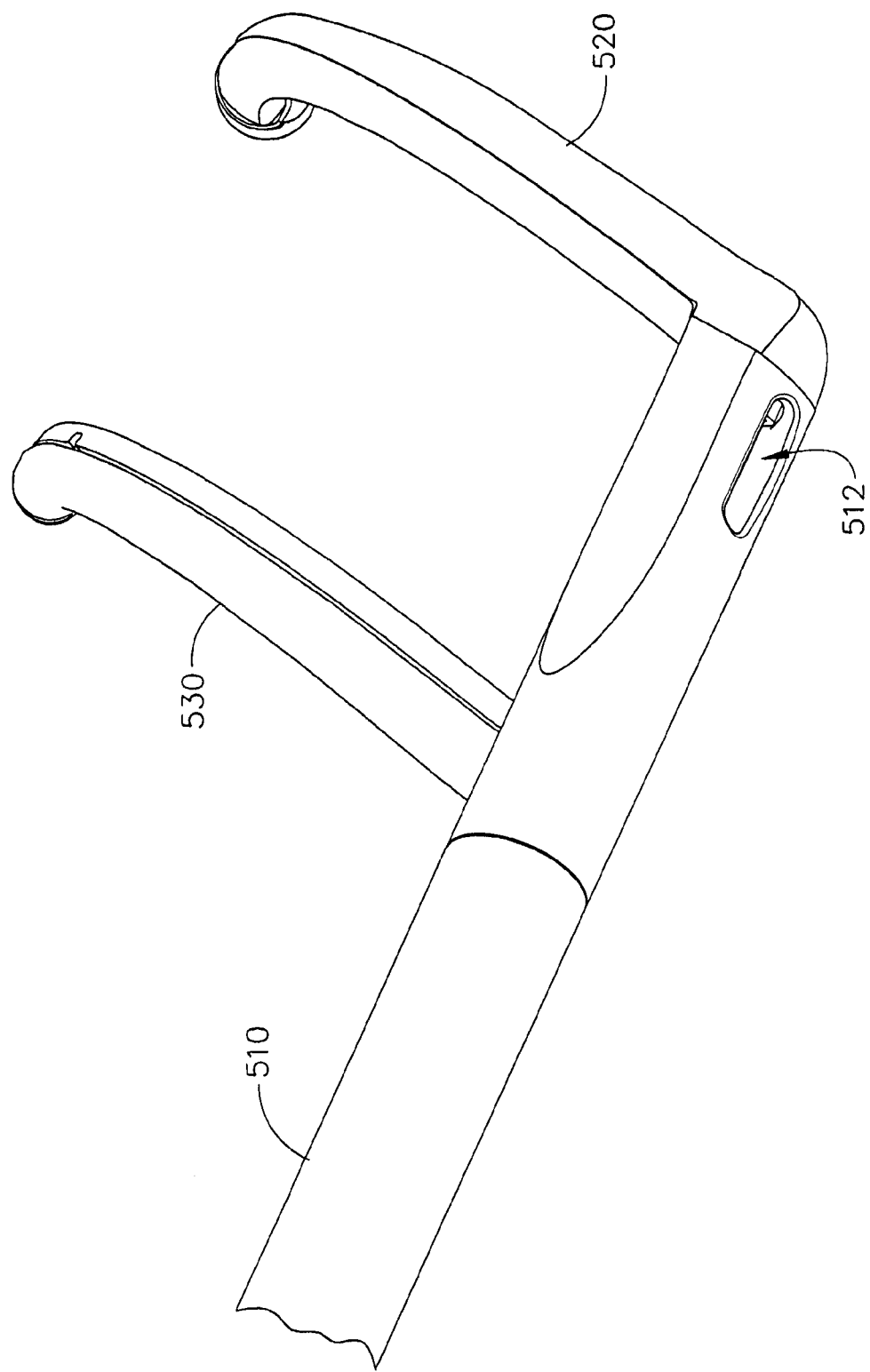
FIG. 12 illustrates an oblique view of the distal end of the articulated clamp of FIG. 9.

FIG. 12 shows an rear view of the distal end of the clamp (500) in the opened position. The shaft (510) includes a weep hole (512) to help drain fluids.

FIGS. 13-16 illustrate an example (700) of means to articulate, open, and close the jaws of a clamp, such as the clamp (500). These figures show a shaft (710), a distal jaw (720), and a proximal jaw (730). An actuator rod (750) is positioned in the shaft (710) and is attached to the proximal jaw (730). Axial movement of the actuator rod (750) is translated to axial movement of the proximal jaw (730). The proximal jaw (730) extends laterally relative the shaft (510) at a constant angle. Connected to the proximal jaw (730) is a guide pin (732) seated in the longitudinal slot (712) in the shaft (710). The guide pin/slot interface prevents the proximal jaw (730) from rotating about the axis of the shaft (710) regardless of the axial position of the proximal jaw (730).

The distal jaw (720) articulates relative the shaft (710) about the pin (722). A locking rod (740) is connected to the distal jaw (720) with the pin (742). A follower pin (744) is attached to the locking rod (740) and is seated in the L-shaped locking slot (714) in the shaft (710) and the stepped follower slot (752) in the actuator rod (750).

Figure 13:
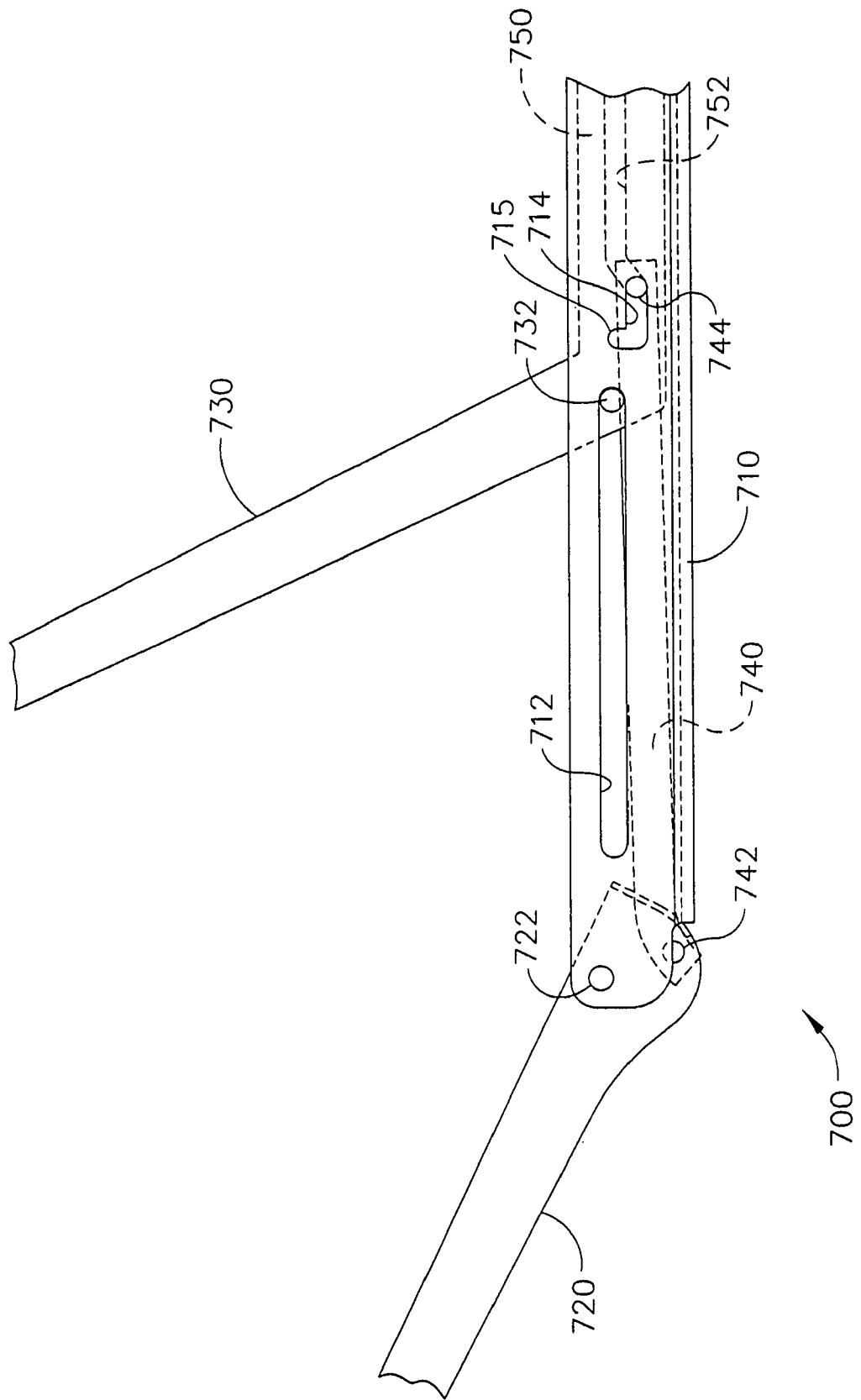
FIG. 13 illustrates a side view of an example of linkages to effect articulation of a clamp.
Figure 14:
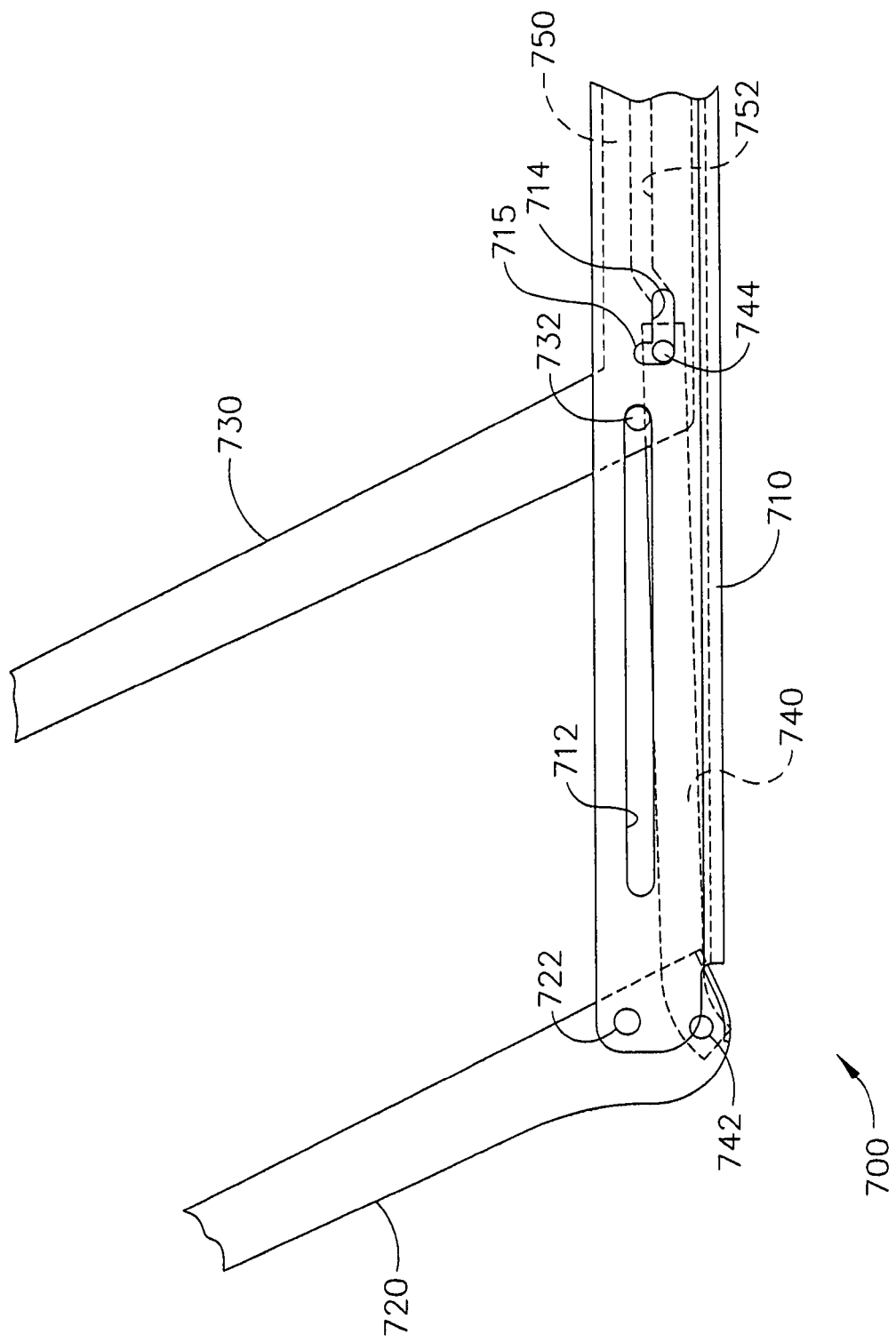
FIG. 14 illustrates a side view of an example of linkages to effect articulation of a clamp.

FIGS. 13 and 14 illustrate the passive articulation of the distal jaw (720) while the actuator rod (750) in its proximal-most position. FIG. 13 shows the distal jaw (720) in its fully articulated position and FIG. 14 shows the distal jaw (720) in its opened position where the jaws are separated and parallel to one another. As the distal jaw (720) articulates, the follower pin (744) moves axially within the limits of the axial leg of the locking slot (714).

Figure 15:
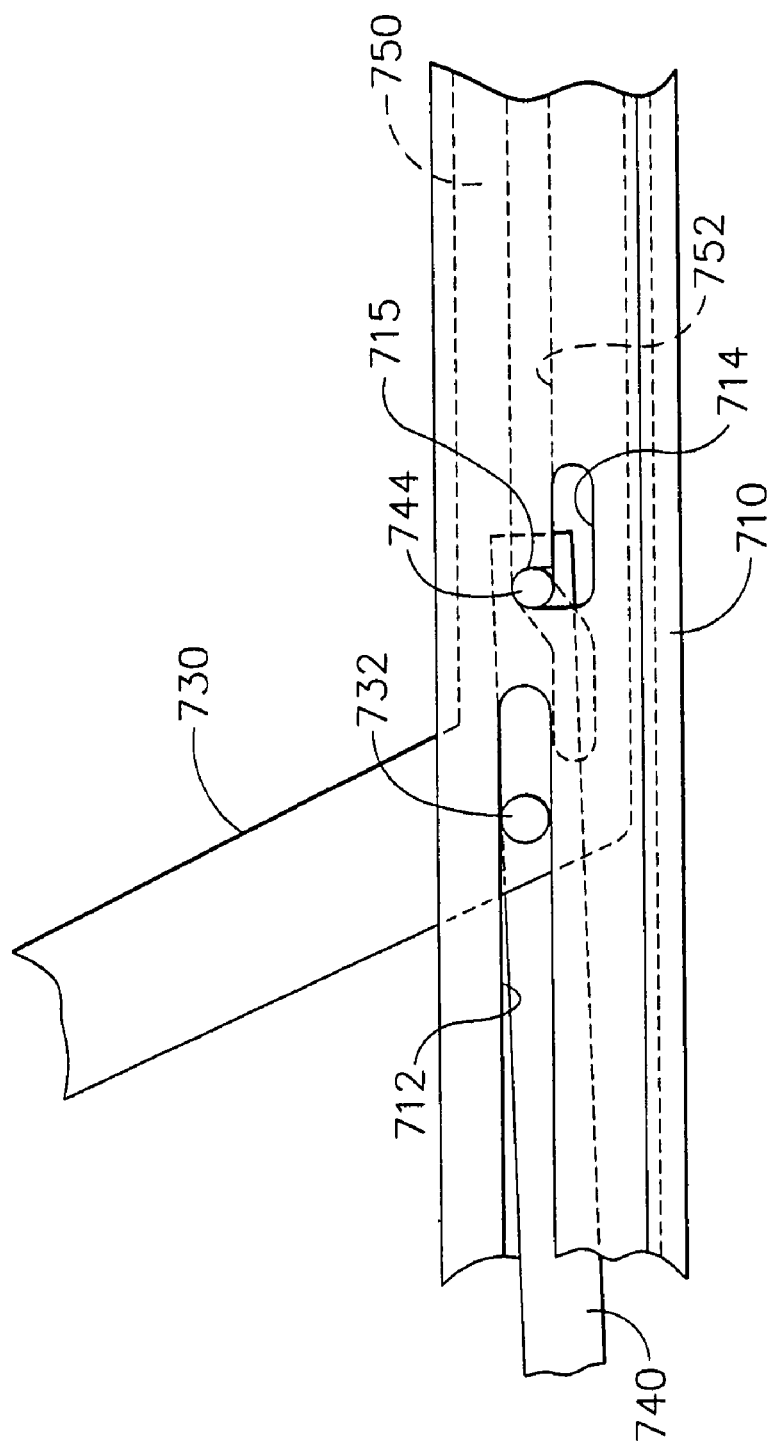
FIG. 15 illustrates a side view of an example of linkages to effect articulation of a clamp.

In FIG. 15 the actuator rod (750) has been moved distally. If the distal jaw (720) is in an articulated position, the step in the follower slot (752) will push the follower pin (744) distally thus articulating the distal jaw (720) to the opened position. The angled step in the follower slot (752) will also push the follow pin (744) upward in the locked portion (715) of the slot (714), as shown in this figure. In this position, axial movement of the follower pin (744) is restricted, thus locking the distal jaw (720) in a position parallel to the proximal jaw (730).

Figure 16:
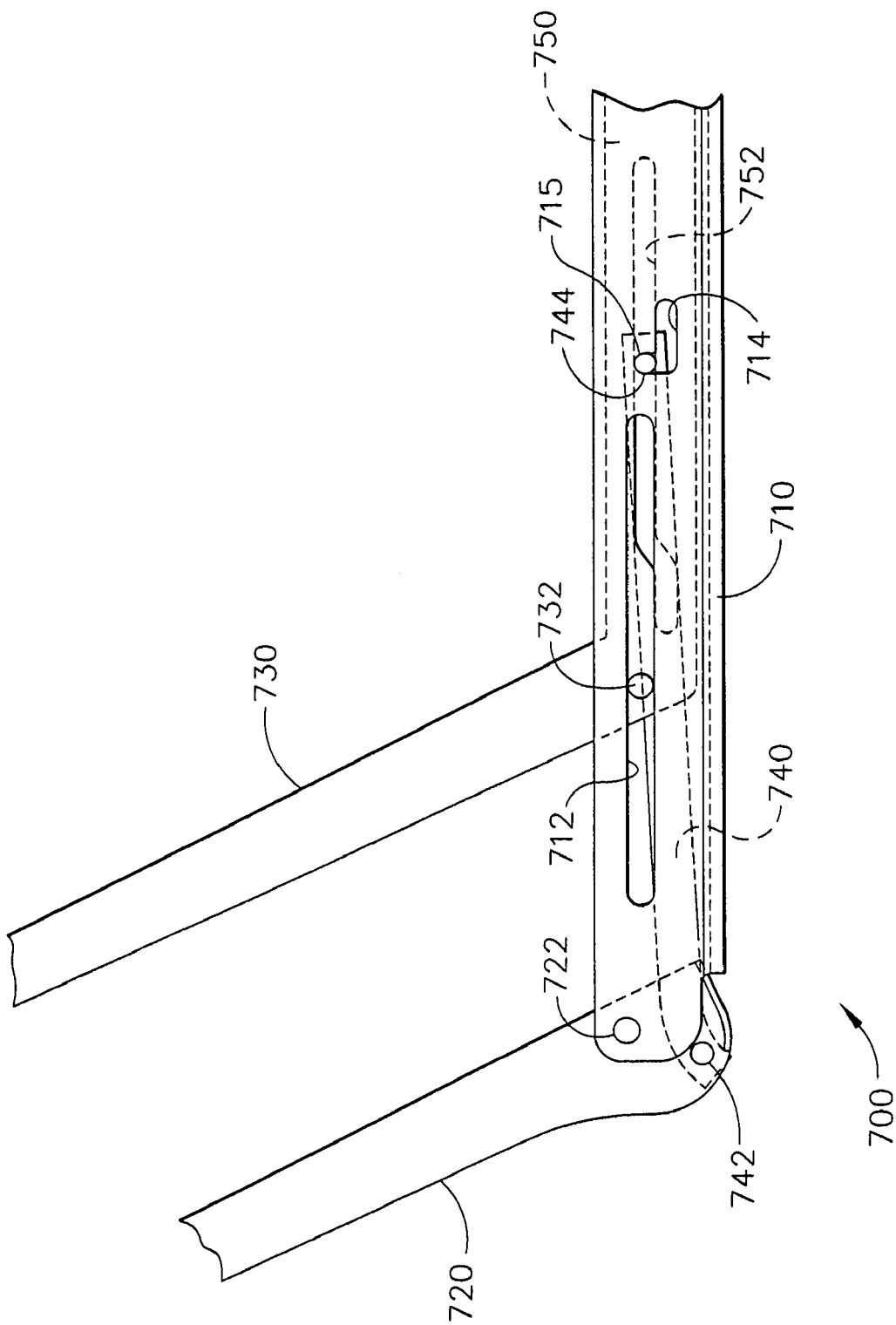
FIG. 16 illustrates a side view of an example of linkages to effect articulation of a clamp.

FIG. 16 illustrates the actuator rod (750) being moved further in the distal direction. The proximal jaw (730) advances towards the closed position. The follower pin (744) remains in the locked position within the locking portion (715). The follower pin (744) is also in the upper step of the follower slot (752) so axial movement of the actuator rod (750) is unrestricted.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:
1. A surgical clamp comprising:
 a) a shaft having a proximal end and a distal end;
 b) a first jaw and a second jaw connected to the shaft for effecting a surgical procedure, the second jaw being pivotably connected to the shaft;

c) a locking member operably connected to the second jaw operable to lock the second law against pivoting motion with respect to the first jaw;

wherein the jaws have respective first and second clamping surfaces and the jaws are operable to assume:

(i) an articulated position wherein the jaws clamping surfaces are separated and not substantially parallel to one another;

(ii) an opened position wherein the jaws clamping surfaces are separated and the second jaw is locked against pivoting motion with respect to the first jaw, with the clamping surfaces substantially parallel to one another; and (iii) a closed position wherein the jaws clamping surfaces are adjacent and the second jaw is locked against pivoting motion with respect to the first jaw, with the clamping surfaces substantially parallel to one another;

the jaws being movable between the opened and closed positions when the second iaw is locked against pivoting motion with respect to the first jaw.

2. The surgical device clamp of claim 1, further comprising an actuator attached to the proximal end of the shaft operable to move the jaws between the closed, opened, and articulated positions.

3. The surgical device clamp of claim 1, wherein the jaws effect tissue ablation.

4. The surgical device clamp of claim 3, further comprising electrodes on the jaws.

5. The surgical device clamp of claim 4, wherein tissue ablation is effected by bi-polar energy.

6. The surgical device clamp of claim 1, wherein in the closed position the clamping surfaces extends laterally from the shaft.

7. The surgical device clamp of claim 1, wherein in the articulated position the second jaw extends distally relative to the shaft.

8. The surgical device clamp of claim 1, further comprising means to articulate, open, and close the jaws.

9. The surgical device clamp of claim 1, wherein at least one of the jaws is curved.

10. The surgical device clamp of claim 1, wherein at least one of the jaws moves toward the closed position by moving axially along the shaft.

11. The surgical device clamp of claim 1, wherein the second jaw articulates relative to the shaft independent of the proximal first jaw.

12. The surgical device clamp of claim 11, wherein the first jaw articulates relative to the shaft independent of the second jaw.

13. A surgical clamp comprising:
a) a shaft;
b) a first jaw connected to the shaft;
c) a second jaw pivotably connected to the shaft, and
d) a locking member operably connected to the second jaw operable to lock the second jaw against pivoting motion with respect to the first jaw;
   wherein at least one of the first jaw or the second jaw is movable toward and away from the other jaw when the second jaw is locked against pivoting motion.

* * * * *

UNITED STATES PATENT AND TRADEMARK OFFICE
CERTIFICATE OF CORRECTION

PATENT NO.       : 7,582,086 B2                                      Page 1 of 1
APPLICATION NO. : 11/254075
DATED            : September 1, 2009
INVENTOR(S)      : Privitera et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 987 days.

Signed and Sealed this

Fourteenth Day of September, 2010

David J. Kappos
*Director of the United States Patent and Trademark Office*